United States Patent [19]

Fagan et al.

[11] Patent Number: 5,720,300
[45] Date of Patent: Feb. 24, 1998

[54] HIGH PERFORMANCE WIRES FOR USE IN MEDICAL DEVICES AND ALLOYS THEREFOR

[75] Inventors: John R. Fagan, Pepperell, Mass.; Lex P. Jansen, Londonderry, N.H.; L. Ven Raman, Framingham; John A. Wright, Jr., Arlington, both of Mass.

[73] Assignee: C. R. Bard, Inc., Murray Hill, N.J.

[21] Appl. No.: 391,010

[22] Filed: Feb. 21, 1995

Related U.S. Application Data

[63] Continuation-in-part of Ser. No. 149,985, Nov. 10, 1993, abandoned.

[51] Int. Cl.⁶ .................................................. A61B 5/00
[52] U.S. Cl. ........................... 128/772; 604/657; 604/658
[58] Field of Search .............................. 606/198; 604/95; 128/772; 148/606

[56] References Cited

U.S. PATENT DOCUMENTS

| Re. 33,911 | 5/1992 | Samson et al. | |
|---|---|---|---|
| 2,358,799 | 9/1944 | Franks . | |
| 3,408,178 | 10/1968 | Myers et al. . | |
| 4,721,117 | 1/1988 | Mar et al. . | |
| 4,748,986 | 6/1988 | Morrison et al. . | |
| 4,922,924 | 5/1990 | Gambale et al. . | |
| 4,998,923 | 3/1991 | Samson et al. . | |
| 5,120,308 | 6/1992 | Hess . | |
| 5,176,149 | 1/1993 | Grenouillet . | |
| 5,365,943 | 11/1994 | Jansen | 128/772 |
| 5,372,144 | 12/1994 | Mortier et al. | 128/772 |
| 5,411,613 | 5/1995 | Rizk et al. | 148/606 |
| 5,415,170 | 5/1995 | Hammerslag et al. | 128/657 |
| 5,449,372 | 9/1995 | Schmaltz et al. | 606/198 |
| 5,465,733 | 11/1995 | Hinohara et al. | 128/772 |

FOREIGN PATENT DOCUMENTS

| 0 395 098 | 10/1990 | European Pat. Off. . |
|---|---|---|
| 0 407 965 | 1/1991 | European Pat. Off. . |
| 0480427 | 4/1992 | European Pat. Off. . |
| 2449759 | 8/1976 | Germany . |
| 1124473 | 5/1989 | Japan . |
| 4210422 | 7/1992 | Japan . |
| 1541072 | 2/1979 | United Kingdom . |
| WO9307303 | 4/1993 | WIPO . |
| WO 95/03847 | 2/1995 | WIPO . |

OTHER PUBLICATIONS

Szombaltfalvy, "Tempering of High–Strength Steel Wires After Patenting and Cold Forming", *Chemical Abstracts*, vol. 83, No. 16, Oct. 20, 1975.

Assefpour–Dezfuly, "Strengthening Mechanisms in Elgiloy", *Journal of Material Science*, vol. 6053, No. 17, 1984.

Assefpour–Dezfuly, "Microplasticity in Elgiloy", *Journal of Materials Science*, vol. 6053, No. 20, 1985.

*Primary Examiner*—Max Hindenburg
*Assistant Examiner*—Pamela L. Wingood
*Attorney, Agent, or Firm*—Arthur Z. Bookstein

[57] ABSTRACT

An elongate flexible wire-like medical device, such as a guidewire for use with a catheter, is formed with a shaft in which the difference between the magnitude of the tensile yield stress and compressive yield stress of the shaft is substantially reduced. The guidewire exhibits superior kink resistance without compromising other desirable characteristics and enables a guidewire to be made in a smaller diameter without loss of performance. The guidewire shaft may be formed from a precipitation hardenable alloy such as an alloy of nickel, cobalt, molybdenum and chromium (MP35N and Elgiloy), 455PH stainless steel or stainless steel alloy 1RK91. Also disclosed is a process for increasing the modulus of elasticity of an alloy of nickel, cobalt molybdenum and chromium. Further, the disclosure relates to an improved management and manufacturing process for constructing the tip of a medical guidewire.

40 Claims, 7 Drawing Sheets

HIGH PERFORMANCE WIRES FOR USE IN MEDICAL DEVICES AND ALLOYS THEREFOR

RELATED APPLICATIONS

This application is a continuation-in-part of U.S. application Ser. No. 149,985 filed Nov. 10, 1993 now abandonned.

FIELD OF THE INVENTION

This invention relates to slender medical devices that must be controllably passed through a tortuous path without permanent deformation including, for example, guidewires used in connection with catheters and, particularly, steerable guidewires used in percutaneous transluminal angioplasty, including coronary angioplasty (PTCA).

BACKGROUND OF THE INVENTION

The invention concerns improvements in medical guidewires and other elongate medical devices that incorporate stiffening elements and in which the device must be controllably passed through a tortuous path without permanent deformation in order that the inserted end of the device can be controlled exteriorly of the patient by the physician. Such wires are used with catheters that may be inserted into a wide variety of blood vessels including, for example, peripheral arteries, coronary arteries and cranial vasculature, among others. The invention further concerns improvements in guidewires adapted for use in coronary angioplasty, in which a stenosed region of a coronary artery is dilated to increase the blood flow through that artery. Because the invention is advantageous with small diameter devices, such as guidewires and the like commonly used in PTCA, the invention and its background are described in that context.

The PTCA procedure typically involves advancement of a guide catheter through a percutaneous puncture in the femoral artery to place the distal end of the guide catheter at the entrance (ostium) to one of the two (right or left) coronary arteries. The guide catheter remains in place throughout the procedure to define a path through which other, smaller diameter angioplasty catheters and guidewires can be advanced to and withdrawn from the coronary arteries. With the guide catheter properly positioned, a balloon dilatation catheter and an associated small diameter, steerable guidewire then are passed through the guide catheter to an ostium of the coronary arteries. The small diameter steerable guidewire is intended to be manipulated into the selected arterial branch and through the stenosis that is to be dilated. After the guidewire has been manipulated and navigated into place through the stenosis, the balloon catheter (in an over-the-wire catheter system) is further advanced over and along the guidewire, with the balloon in a deflated state to place the balloon within the stenosis. The balloon then is inflated under substantial pressure to dilate the stenosed region of the artery. The effective placement of the guidewire is critical to the success of the procedure. If the guidewire cannot be navigated to and through the stenosis, the balloon cannot be guided into the stenosis and the stenosis cannot be dilated.

Numerous difficulties are presented in the design of a small diameter steerable guidewire such as that intended for use in PTCA. The difficulties may be better appreciated from an understanding of the human arterial anatomy from the usual point of entry, the femoral artery in the groin region, to and including the coronary arteries. The portion of that arterial anatomy is illustrated in fragmented, somewhat diagrammatic, fashion in FIG. 1. The arterial system carries blood from the heart 10 through the aorta 12 in a direction indicated by the arrows 13. The arterial system leading from the heart 10 includes, in a downstream direction, the ascending portion 14 of the aorta, the aortic arch, indicated generally at 16, and the remaining (descending) portion 18 of the aorta. Numerous arteries branch off the aorta to carry blood to the internal organs of the body as well as the limbs and extremities. The coronary artery system (suggested schematically and in part at 20) through which oxygenated blood is directed back to the heart tissue itself includes two main arteries, a left main coronary artery 21 and a right coronary artery 22, both of which branch off the ascending portion 14 of the aorta immediately downstream of the heart. Each of the left and right coronary arteries 21, 22 leads to a system of numerous branch arteries, some of which are suggested schematically at 20A, 20B, 20C, 20D, that spread out over and through the wall of the heart muscle thereby serving to distribute oxygenated blood and nutrients to the entire heart muscle. The object of the PTCA procedure is to treat the portion of a coronary artery that has developed a stenosis, for example, as suggested at 23, that obstructs blood flow through that portion of the artery. In the PTCA procedure the region of the stenosis 23 is dilated to enlarge the flow area and improve the flow of blood to those portions of the heart tissue served by the stenosed artery.

The PTCA procedure involves initial placement of a comparatively large diameter (0.078–0.117 inch outer diameter) guide catheter 24 through a percutaneous puncture (not shown) in the femoral artery 19. The guide catheter 24 has a specially formed distal end that facilitates engagement of the tip 26 of the guide catheter with the entrance (ostium) 28 to one or the other of the main coronary arteries 21, 22.

In a common type of guide catheter (Judkins-left) the distal end has primary and secondary curves 30, 32 that may have a radius of the order of one-half to one inch as compared to the radius of the order of one and one-half to two inches for the curve that may be assumed through the aortic arch.

The guide catheter 24, once placed, defines a path through and along which an angioplasty catheter (which typically is far more flexible than the guide catheter and about 0.040 inch diameter or less) and its associated guidewire can be advanced easily and quickly to the entrance 28 of the coronary artery. The procedure for placing the guide catheter is well-known to those familiar with the art.

In a typical procedure, a small diameter (less than about 0.020 inch and preferably of the order of 0.018 inch or less and most commonly about 0.014 inch) steerable guidewire, indicated generally at 34 (FIG. 1) is preloaded into the receptive guidewire lumen (not shown) in the balloon angioplasty catheter, indicated generally at 36. The guidewire is longer (e.g., 175 cm) than the catheter (e.g., 145 cm). The angioplasty catheter 36 and guidewire 34 are advanced together through the previously placed guide catheter 24 to the ostium 28. Then, while holding the balloon catheter 36 in place within the guide catheter 24, the guidewire is advanced through the balloon catheter into the coronary arteries. The slender guidewire is manipulated from its proximal end 35 by the physician while the patient is under fluoroscopy so that the distal end of the guidewire can be observed fluoroscopically. The physician, by combined rotational and longitudinal movements of the guidewire 34, must steer the guidewire 34 through the branches of the coronary arterial tree so that the distal end 37 of the guidewire passes through the stenosis 23. Once so positioned the guidewire 34 is held stationary by the physician or an assistant and the balloon catheter 36 then is advanced over and along the guidewire 34, thereby guiding the balloon 40 of the catheter 36 directly to the stenosis 23. With the balloon in place, it then is inflated through an inflation lumen 42, typically with a liquid under high pressure, to forcibly dilate the stenosis.

It should be understood that for ease of illustration, the stenosis 23 in FIG. 1 has been shown as in a location in the arterial tree that is relatively free of complex tortuousities and is relatively close to the coronary ostium. In order for the guidewire to effectively serve its function of guiding the balloon catheter to the stenosis, the guidewire should be capable of being steered and manipulated into any of the arterial branches such as suggested schematically at 20A–20D as well as other branches located at the most distal portions of the coronary arterial tree. Frequently the stenosis will be located well within a highly tortuous arterial branch of the coronary anatomy such as suggested at 23B in branch artery 20B. In order to reach and treat a stenosis so located, it will be appreciated that the balloon catheter and the guidewire must be steered and advanced through the tortuous anatomy along a path suggested in phantom at 34B in FIG. 1.

In order for the guidewire to perform its function effectively, it should have a number of characteristics. The guidewire should have adequate longitudinal flexibility to enable it to conform to the various curves of the patient's arteries including the frequently highly tortuous configuration of the coronary arteries. It should have adequate longitudinal stiffness to have sufficient column strength so that it can be pushed, as it is advanced through the arteries, without buckling. In order that the guidewire may be steered controllably, it should be sufficiently torsionally rigid to be able to transmit controllably to its distal end substantially all of the rotation applied at the proximal end. Although the guidewire must have adequate column strength to be pushable without buckling, the distal region of the guidewire should be soft and flexible to reduce the risk of injury to the delicate inner lining of the artery. The guidewire also should be kink resistant. Kinking (permanent deformation) in the guidewire typically results in aberrant, uncontrolled whipping movement at the distal tip of the guidewire rather than the desirable controlled transmission of rotation. The guidewire also desirably is highly radiopaque at its distal tip in order that its movement and position may be readily observed under fluoroscopy. Also important among the characteristics of a guidewire is that it have a good tactile response in order that the physician may feel, at the proximal end of the guidewire, events occurring at the distal end.

Since the development of the first small diameter steerable guidewire (see U.S. Pat. No. 4,545,390 to Leary) a primary focus in the continued development of small diameter steerable guidewires has been to reduce the diameter of the guidewire without adversely affecting its performance. A reduction in guidewire diameter is significant because it enables the catheter itself to be made in a smaller diameter. That, in turn, enables the catheter to be advanced into tighter stenoses and smaller diameter arteries. Efforts to improve small diameter steerable guidewires, either by reducing the diameter or otherwise, have involved trade-offs and compromises among the desirable characteristics described above.

Some guidewires have been formed from a superelastic alloy such as a nitinol (nickel-titanium) alloy. The superelastic characteristic of the material provides for excellent kink resistance and a desirably soft, flexible distal tip. Representative of such guidewires are those described in U.S. Pat. No. 4,925,445 (Sakamoto). The advantages of such superelastic guidewires have been achieved, however, at the expense of other desirable characteristics, particularly in small diameter guidewires of the type now commonly used in PTCA, of the order of 0.014 inch. Although the performance of superelastic guidewires may be less problematic in larger sizes, the performance may become marginal when the diameter is as small as 0.014 inch and poor in smaller sizes. Performance becomes marginal to poor, particularly with respect to the column strength of the guidewire and its ability to be pushed without buckling. Similarly, superelastic guidewires of the order of 0.014 inch diameter and smaller, adapted for use in PTCA tend to display marginal to poor steerability characteristics. These disadvantages also compromise the tactile response of the wire.

In order to achieve improved column strength, it has been proposed to make guidewires from tungsten or a tungsten alloy. Although such a guidewire results in improved column strength (sometimes referred to as "pushability") it does so at the expense of flexibility and kink resistance.

To date, the most commonly used material for small diameter steerable guidewires, has been type 302 or 304 stainless steel because it appears to have been the most acceptable compromise. Among the compromised features in a stainless steel guidewire is its diameter. Typically, guidewires that have been made in diameter less than 0.014 have exhibited marginal to poor performance and have found considerably less use.

It would be desirable to provide a small diameter steerable guidewire in which the foregoing desirable characteristics are maximized, with a minimum amount of compromise of one characteristic for another. It also would be desirable to provide a small diameter steerable guidewire in still smaller diameters than those presently in use without sacrificing performance. It is among the objects of the invention to provide such a guidewire.

SUMMARY OF THE INVENTION

The present invention is based, in part, on a recognition as to the manner in which a medical guidewire becomes kinked and in the construction of the guidewire to avoid such kinking. In particular, a guidewire in accordance with the invention is formed from an alloy having a modulus of elasticity that is at least about that of stainless steel and has been worked and treated to have a more balanced stress/strain curve, that is, a stress/strain curve in which the magnitude of the compressive yield strength is substantially closer to that of the tensile yield strength than has been the case with prior guidewires. Ideally, the guidewire shaft is formed from wire of an alloy in which the compressive and tensile yield stresses are approximately equal during bending. Desirable materials for practising the invention may include a number of specially treated precipitation hardened alloys including, for example, alloys commercially available under the trade designations MP35N, Elgiloy, 455PH and Sandvik 1RK91.

More specifically, it has been determined that when a guidewire becomes permanently deformed in use, it generally fails in compression, not in tension. When a guidewire is advanced through a right bend or tortuous arterial anatomy, the radially inward side of the guidewire shaft at the region of the bend is compressed while the radially outward side is in tension. If the radius of the bend is so small as to stress the material beyond its elastic limit, the wire will deform permanently, forming a permanent kink that will impair the subsequent functioning of the guidewire. The present invention is based, in part, on a recognition that the wires that have been used for forming guidewire shafts typically are weaker in compression than in tension. Generally, the yield stress (the point at which permanent deformation results) in compression for such wires typically has been substantially less than that of the yield stress in tension. The magnitude of the compressive yield stress (and corresponding strain at the yield point) may be of the order of 60% that of the tensile yield stress and corresponding strain. When the guidewire is bent, as when passing through curved anatomy, the stresses on the outside and the inside of the curve increase equally as the degree of bend increases. The guidewire fails prematurely in compression because the compressive yield stress, on the inside of the bend, is reached before the tensile yield stress, on the outside of the bend, is reached.

An important aspect of the invention concerns the provision of a guidewire in which the guidewire shaft is formed so that its tensile yield stress (and corresponding strain at yield) and compressive yield stress (and corresponding strain at yield) are substantially less disproportionate. Thus, when the guidewire is bent, it will remain elastic through a greater range of stresses than with prior guidewires in which the compressive stress prematurely reaches the point of failure. With the present invention, compressive failure is delayed enabling the wire to be bent in a sharper curve without permanent deformation.

Among the exemplary alloys that may be used in the practice of the invention is a precipitation hardenable alloy of nickel, cobalt, molybdenum and chromium commercially designated as MP35N. The wire that is to form the shaft of the guidewire is cold worked, by drawing through dies, to an extent sufficient to raise its tensile strength to a desired level. The wire then is cut to a desired length and is straightened using conventional wire straightening techniques. In this state, the wire can be heat treated at selected temperatures for a time period sufficient to cause the alloy to become precipitation hardened to the extent desired. The manufacture of the guidewire shaft can be controlled such that the precipitation hardened alloy exhibits a more balanced stress/strain curve in which the magnitudes of the compressive and tensile yield points are substantially closer to each other than had been the case with prior guidewire shaft materials. Consequently, the magnitudes of the compressive and tensile yield stresses are closer. The magnitude of the compressive yield stress may be of the order of 85% of the tensile yield stress. Similarly, the more balanced nature of the stress strain curve may be demonstrated by a comparison of the compressive and tensile strains at yield. With the present invention, the magnitude of those strains is substantially closer than with the prior art.

The heat treatment for each of the above alloys serves not only to precipitation harden the alloy, to make it stronger, but also serves to partially relieve internal stresses in the alloy that were developed during the cold working of the metal. By relieving some of the internal stress, the wire is less likely to become seriously deformed during subsequent manufacturing steps, such as centerless grinding.

Additional exemplary alloys that can be treated to a state where they are precipitation hardened sufficiently to define less disproportionate yield points include an alloy composed of nickel, cobalt, molybdenum and chromium having a small amount of iron, such alloy being commercially available under the trade designation Elgiloy from Elgiloy, Incorporated, Elgin, Ill. Still another exemplary alloy is that commercially available under the designation 455PH from Carpenter Steel Co. of Reading, Pa. That alloy is a single stage martensitic precipitation hardenable stainless steel, modified by changing the proportions of chromium and nickel and further modified by adding copper and titanium. Still another exemplary precipitation hardenable alloy is that commercially available from Sandvik Steel of Scranton, Pa. under the trade designation Sandvik steel 1RK91 (believed to be described in PCT patent application No. PCT/SE92/00688, Int'l. Publication No. WO 93/07303).

Another aspect of the invention relates to the discovery that for MP35N, and possibly for Elgiloy, the heat treatment surprisingly increases its modulus of elasticity.

By constructing a guidewire shaft in accordance with the invention, the guidewire shaft can be made in a smaller diameter without loss of desirable performance characteristics including resistance to kinking, stiffness (column strength) and torque transmission, among others. That, in turn, allows the use of smaller diameter catheters. Alternately, if the shaft diameter is not reduced, a guidewire made in accordance with the invention can be expected to exhibit improved operating characteristics as compared to an identical guidewire constructed of conventional stainless steel wire.

In another aspect the invention, an improved It is among the general objects of the invention to provide a guidewire construction by which the guidewire can be made in a smaller diameter without significant loss of performance.

Another object of the invention is to provide a guidewire having an ideal combination of characteristics without adversely compromising certain of the desirable guidewire characteristics in favor of others.

A further object of the invention is to provide a guidewire having a superior combination of pushability, rotational transmission and kink resistance.

Still another object of the invention is to provide a guidewire shaft having a more balanced stress/strain curve than guidewires of the prior art.

A further object of the invention is to provide a technique in which the modulus of elasticity of selected alloys may be increased by selective heat treatment.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 2:
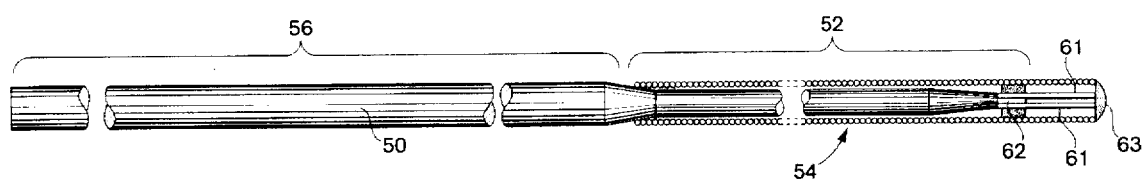
FIG. 2 is a fragmented, partly sectioned illustration of a common form of guidewire with which the invention may be used.

Guidewires embodying the invention may include a wide range of guidewire constructions. A typical guidewire construction, illustrated generally in FIG. 2, includes an elongate, flexible, torsionally rigid shaft 50 in which a distal segment 52 of the shaft is of reduced diameter to increase its longitudinal flexibility. The reduced diameter distal segment of the shaft typically may be contained within a flexible helical coil 54 or other covering. Representative of such guidewire constructions are those disclosed in U.S. Pat. Nos. 4,545,390 (Leary); 4,763,647 (Gambale); 4,922,924 (Gambale et al.) and 5,063,935 (Gambale), the disclosures of which are incorporated herein by reference.

Figure 1:
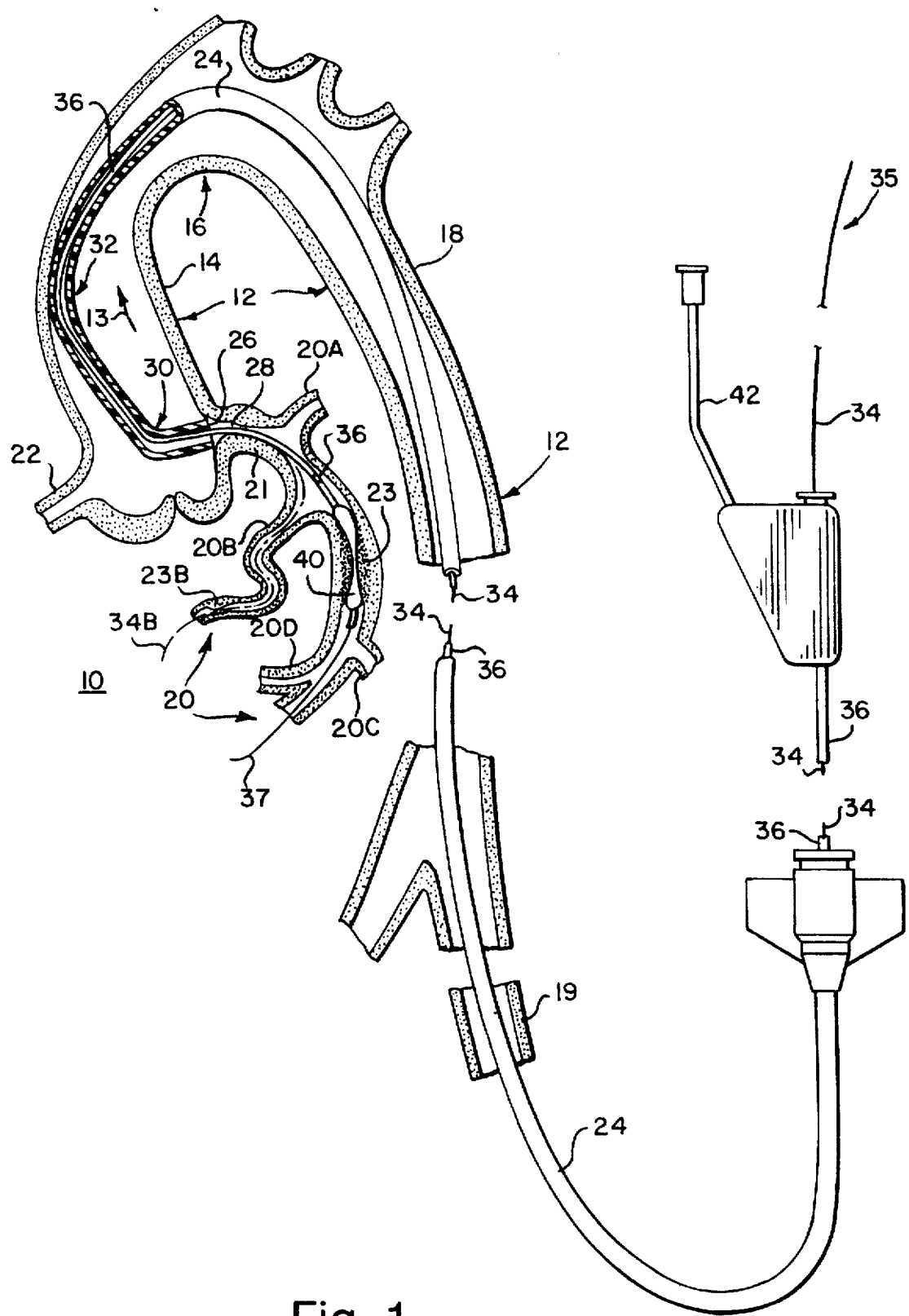
FIG. 1 is a fragmented, somewhat diagrammatic, illustration of the human arterial and coronary anatomy with an angioplasty apparatus of a guide catheter, a balloon angioplasty catheter and a guidewire in place to perform an angioplasty.

In a guidewire used for percutaneous transluminal coronary angioplasty, a typical length for the guidewire is of the order of 175 centimeters. That is sufficiently longer than the catheter with which the guidewire is to be used so that the distal end of the guidewire can extend distally beyond the distal end of the catheter while the proximal end of the guidewire can be grasped and manipulated by the physician. The guidewire shaft may be considered as having a substantially uniform diameter proximal segment 56, that may range from about 0.010 inch to about 0.018 inch in diameter. The reduced diameter distal segment 52 may terminate at its end 62 in a diameter of the order of a few thousandths of an inch. The coil 54 typically is attached at its end regions to the shaft 50. The distal segment 52 may terminate short of the distal end of the coil and may be connected to the distal end of the coil by one or more slender safety ribbons 61. The safety ribbon 61 is attached at one end to the distal segment and at its other end to the tip weld 63 formed at the distal tip of the coil 54. The length of the distal segment and helical coil may vary from about 15 centimeters to about 40 centimeters long. The distal segment 52 is intended to be more flexible, longitudinally, than the proximal segment in order that the distal segment can accommodate the bends that must be traversed through the aortic arch, the primary and secondary curves 30, 32 of the guide catheter and the sometimes tortuous anatomy of the coronary arteries, as illustrated somewhat diagrammatically in FIG. 1.

Figure 2A:
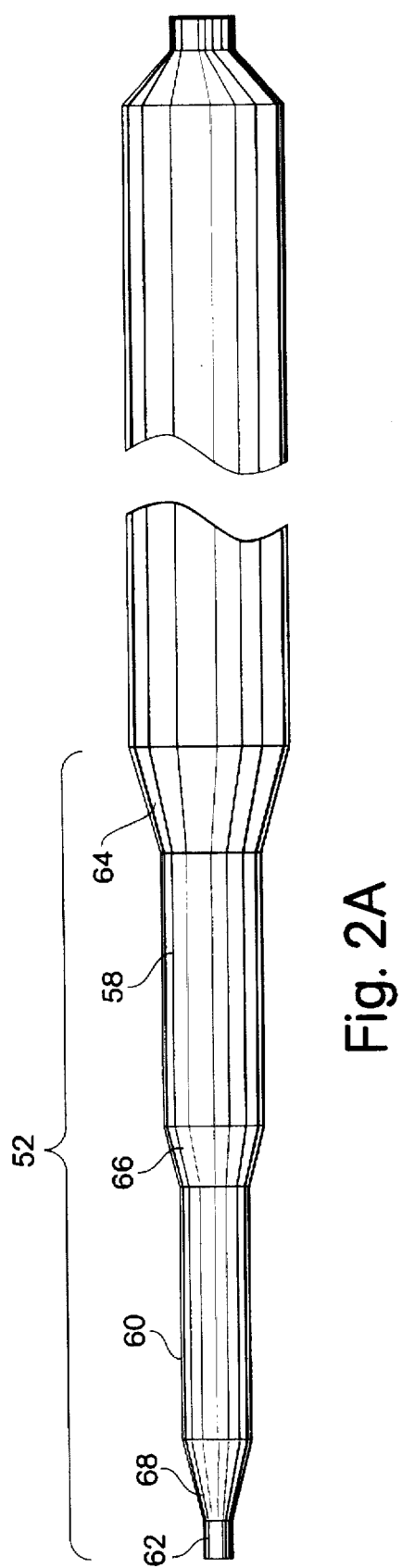
FIG. 2A is a fragmented, greatly enlarged illustration of a guidewire shaft having a reduced diameter (step tapered) distal shaft segment.

FIG. 2A illustrates a typical guidewire shaft geometry. The shaft is formed from wire having a diameter of between 0.010 to 0.018 inch, most commonly 0.014 inch. The distal segment 52 of the shaft is reduced in diameter, typically by centerless grinding. The distal segment 52 of the shaft may be formed in a continuous taper or in a step tapered arrangement, as illustrated in FIG. 2A. For example, the distal segment of the shaft may be centerless ground to form a series of progressively reduced diameter barrel segments 58, 60, 62 alternated with tapered segments 64, 66, 68. The number of barrel and taper segments, as well as their respective lengths, may be varied to provide different flexibility and torsional characteristics for the distal segment 52 of the guidewire as may be desired.

It should be appreciated that the guidewire may include a construction in which the flexibility of the distal segment increases in a distal direction in order to enable that portion of the guidewire to more readily flex to accommodate tortuous arterial anatomy that can be expected to be encountered within the coronary arteries. Typically, the length for the distal segment is selected so that the most flexible portions of the guidewire can be inserted deeply into the coronary arteries should that be desired. Among the difficulties presented by increasing the flexibility at the distal portion of the guidewire is that in so doing, the ability for the guidewire to transmit rotation from its proximal end to its distal end may be compromised. Also, among the significant difficulties encountered in the use of such guidewires is that if any portion of the guidewire becomes kinked, and especially if a kink develops in the distal region, the ability for the wire to controllably transmit rotation from the proximal to the distal end is destroyed and the guidewire loses its steerability. Steerability is essential if the guidewire is to be successfully navigated through the coronary arterial tree to the location of the stenosis to be treated. It is not uncommon to encounter a tortuous anatomy having small radius curves or bends such that when it is attempted to advance the guidewire through the bends, the guidewire is stressed beyond its elastic limit, resulting in plastic deformation of the guidewire shaft and a resulting kink. When that occurs, the controllability of the guidewire is lost and it may be necessary to remove the guidewire and replace it with one that is undamaged.

Prior art guidewires have been proposed to provide maximum stiffness and torsional rigidity by forming the guidewire shaft from a very stiff material such as tungsten. Although a shaft formed from a tungsten alloy will display superior rigidity and column strength, it performs poorly in kink resistance, flexibility and ability to controllably navigate through tortuous anatomy. Guidewires also have been proposed and made in which the shaft is formed from a superelastic alloy, such as a nickel-titanium alloy (nitinol). While such superelastic alloys result in a guidewire having superior kink resistance, the modulus of elasticity of such alloys typically is low. A guidewire in which the shaft is formed from a superelastic alloy can be expected to exhibit superior flexibility and kink resistance but also can be expected to exhibit poor column strength, poor torsional rigidity and, consequently, poor steerability. Additionally, nitinol is not easily adapted to conventional metal joining techniques such as welding, brazing or soldering. That presents difficulties in manufacturing. Consequently, guidewire design and construction has been a compromise among the varying desirable properties. Stainless steel (types 302 and 304) appears to have presented the best compromise and has been, generally, the material of choice for medical guidewires for many years.

Figure 4:
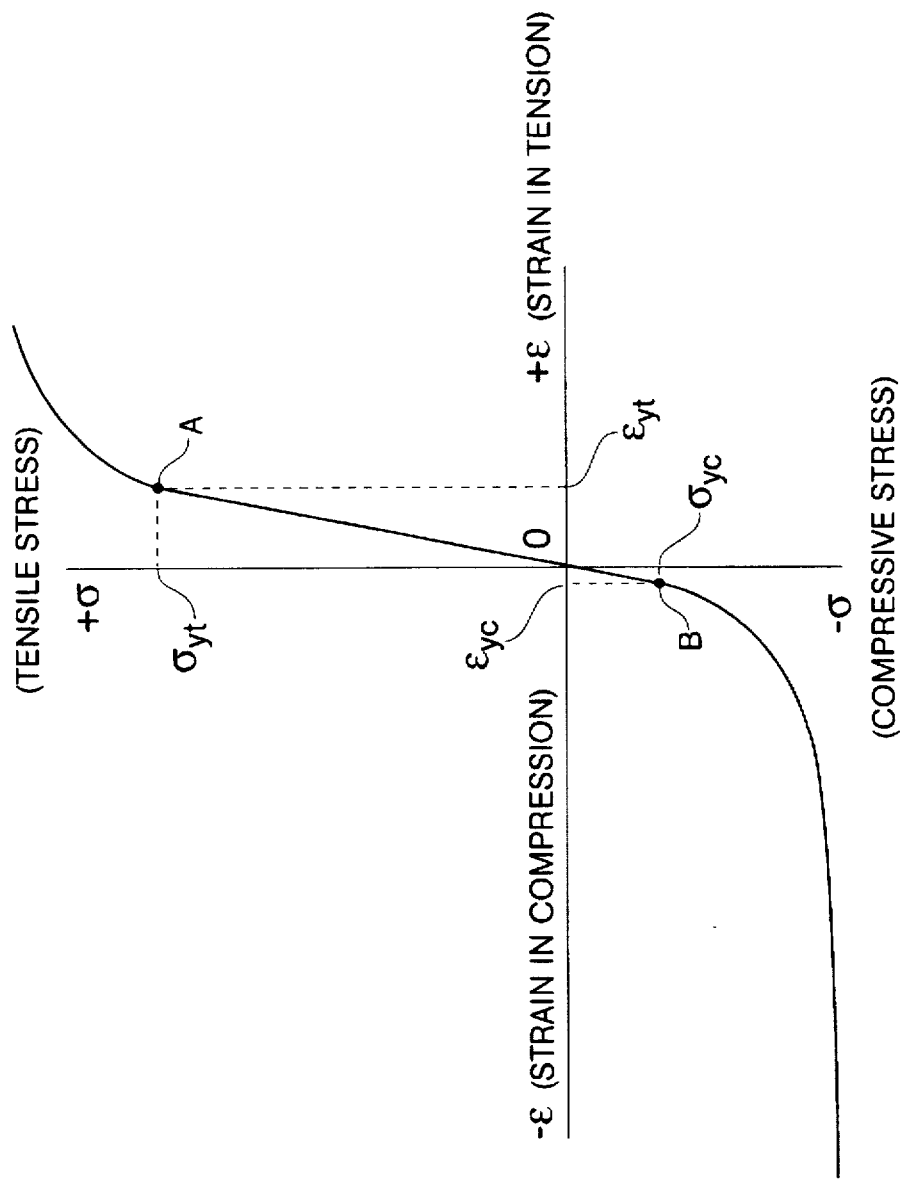
FIG. 4 is a diagrammatic illustration of the stress/strain curve of a typical prior art guidewire having a shaft formed from cold drawn stainless steel.

With the conventional material used to make a guidewire shaft (e.g., cold worked stainless steel wire), the location of the yield point on the stress/strain curve is substantially closer to zero on the compression leg of the curve than on the tension leg of the curve. Consequently, the magnitude of the yield stress (and the yield strain) of the alloy is substantially less in compression than it is in tension. That is a common characteristic of stainless steel wire that has been cold worked by drawing it through a reduced diameter die which dramatically increases the dislocation density in the alloy. Although such cold working is important in order to increase the strength of the stainless steel wire, it has adverse consequences. In particular, by cold working the wire in tension to effectively increase its tensile strength, the compressive strength is reduced. This phenomenon, in which cold working to increase the strength in one sense can cause a reduction of strength in the opposite sense, is sometimes referred to as the Bauschinger effect. The degree to which the strength reduction occurs is a function of the degree of cold working to which the wire is subjected. Thus, a stainless steel wire that has been cold worked to increase its tensile strength by drawing it through a die can be expected to have a stress/strain curve with the characteristics illustrated diagrammatically in FIG. 4. That stress/strain curve may be considered as disproportionate. Point A in FIG. 4 represents the tensile yield point of the wire, that is, the stress and strain at which plastic deformation begins to occur in tension. Point B in FIG. 4 illustrates the yield point along the stress/strain curve at which plastic deformation begins to occur in compression. It will be apparent that for such cold worked stainless steel wire the magnitude of the yield stress $\sigma_{yc}$ and yield strain $\epsilon_{yc}$ in compression (Point B) is substantially less than the magnitude of the yield stress $\sigma_{yt}$ and yield strain $\epsilon_{yt}$ in tension (Point A). The yield point along the stress/strain curve may be located so that the compressive yield stress may be of the order of about 50%–60% of the tensile yield stress. For example, the Metals Handbook, 8th Edition, Vol. 1, American Society of Metals at page 503 indicates that for Type 301 autenitic stainless steel, having been cold worked to a half-hard state, the design yield stress is in tension and compression, at room temperature are about 110,000 p.s.i. and about 55,000 p.s.i., respectively. Consequently, when a guidewire with substantially disproportionate yield points is subjected to a bend that will tend to cause it to fail, the failure of the material will occur in compression.

It will be appreciated that when a guidewire shaft is subjected to bending, the stresses developed in the guidewire at the region of the bend follow a gradient in which the portion of the wire that is disposed on the outside of the bend is subjected to a maximal tensile stress while the portion of the wire at the inside of the bend is subjected to a maximal compressive stress that, before failure, is equal in magnitude but opposite in direction to the tensile stress on the outside of the bend. Thus, when a guidewire shaft is formed so that it has a lower compressive yield stress than its tensile yield stress, the compressive yield stress will be reached before the tensile yield stress. That will result in premature failure of the wire as has been typical in the prior art.

Figure 3:
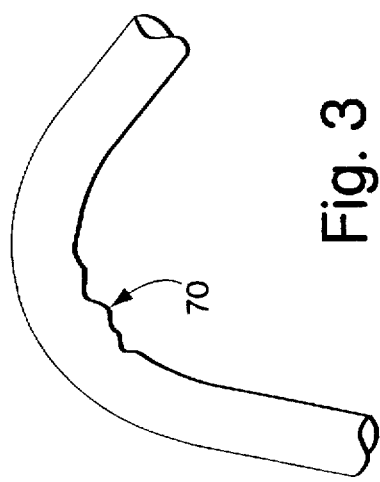
FIG. 3 is a somewhat diagrammatic illustration of a portion of a guidewire shaft that has been subjected to a sharp bend with the guidewire having failed in compression on the inside of the radius of the bend.

FIG. 3 illustrates, in exaggerated, diagrammatic detail, the manner in which a wire formed from conventional material (e.g., stainless steel) fails in compression, on the inside 70 of the curve. Such failure, of course, results in permanent deformation of the wire and the loss of the ability to effectively control the steerability of the wire.

A significant aspect of the invention resides in forming the guidewire shaft so that the difference between the magnitude of the tensile yield stress $\sigma_{yt}$ (and corresponding degree of strain $\epsilon_{yt}$) and compressive yield stress $\sigma_{yt}$ (and corresponding degree of strain $\epsilon_{yt}$) is significantly less disproportionate than the prior art stainless steel wires. Although ideally the yield stresses should be the same, to do so would require excessive heat treatment that could approach a fully annealed condition that, in turn, would adversely affect the overall strength and performance of the wire.

In the present invention, the guidewire shaft is formed so that the Bauschinger effect is reduced substantially. The shaft of the guidewire is formed so that the magnitude of its compressive yield stress and tensile yield stress, and their corresponding degrees of strain at the compressive and tensile yield points, are substantially less disproportionate. With the present invention, it may be possible to raise the compressive yield stress to about 85% of the tensile yield stress.

Figure 5:
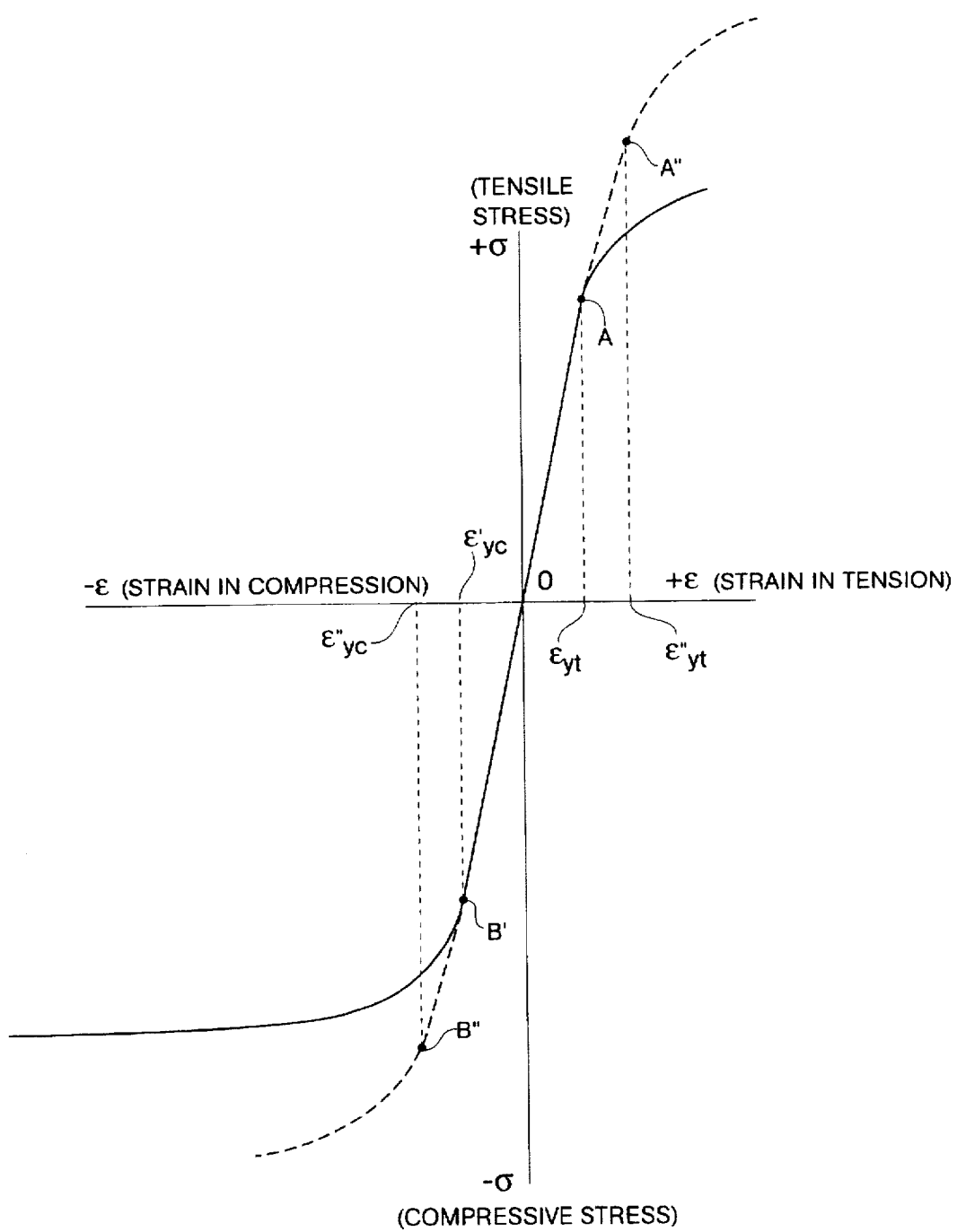
FIG. 5 is a diagrammatic illustration of a balanced stress/strain curve in accordance with the invention and illustrating further, in phantom, the additional strength that may be obtained in the practice of the invention.

FIG. 5 illustrates the stress/strain curve of a wire in accordance with the invention in which the magnitude of the tensile yield stress and strain at yield point A is substantially less disproportionate with respect to the compressive yield stress and yield strain at yield point B' than is the case with prior art stainless steel guidewires (e.g., FIG. 4). With such a wire, the length of the linear portion of the compressive segment (line OB') of the stress/strain curve, representing elastic behavior, is substantially closer to that of the tension segment (line OA). The use of a guidewire shaft having such characteristics results in a guidewire having an ability to resist kinking even when passed through sharply tortuous bends and without sacrificing the ability to torsionally control the guidewire. A guidewire so made can be constructed in a smaller diameter while achieving the same level of performance as had been achieved with guidewires in the prior art. If made in the same diameter as a prior art wire, it will exhibit superior performance.

FIG. 5 further illustrates, in phantom, a stress/strain curve for heat treatable precipitation hardening alloys that can be processed to display not only a more balanced stress/strain curve, but also one in which the yield points, A", B" both in tension and in compression are further increased to substantially enhance the strength of the guidewire shaft. The stress/strain curve for a material selected and treated in that manner is illustrated in phantom in FIG. 5.

In the preferred embodiment of the invention, the foregoing characteristics may be achieved by making the guidewire shaft from a precipitation hardened alloy. Alloys found to be suitable include an alloy of nickel, cobalt, molybdenum and chromium, commercially available under the designation MP35N from Fort Wayne Metals of Fort Wayne, Ind. Also useful in the practice of the invention is a similar alloy that contains a small amount of iron and is commercially available under the trade designation Elgiloy from Fort Wayne Metals and Carpenter Steel Company of Reading, Pa. Other materials usable in the practice of the invention include a single stage martensitic precipitation hardenable stainless steel having modified proportions of chromium and nickel and with additional elements of copper and titanium, commercially available from Carpenter Steel Co. under the designation 455PH. Also usable in the practice of the invention is a precipitation hardenable steel available under the trade designation 1RK91 from Sandvik Steel. These alloys are characterized in that they are precipitation hardenable by controlled heat treatment, not only to increase the tensile strength of the material but also to increase the compressive yield stress (and corresponding strain at yield) so that it is not substantially disproportionate to the tensile yield stress (and corresponding strain at yield).

By way of one specific example, when forming a guidewire shaft from an alloy of nickel, cobalt, molybdenum and chromium (MP35N), the alloy may be obtained in the form of cold dram wire having a tensile strength as low as about 150,000 p.s.i., but preferably about 250,000 p.s.i., and a modulus of elasticity comparable to type 304 stainless steel (about 28,000,000 to 29,000,000 p.s.i.), the wire having been cold worked to about 55% reduction from the penultimate to the ultimate drawing die. The wire so obtained then is subjected to heat treatment at about 1200° F. for about thirty minutes. The heat treatment causes the alloy to precipitation harden to a tensile strength of about 300,000 p.s.i., an increase, in this instance, of about 20%. It should be understood, however, that this is but one example of a variety of precipitation hardenable alloys having different characteristics of cold working, tensile strength and chemical composition before being treated to a precipitation hardened state. It also should be understood, that in the practice of the invention, those characteristics should be selected in conjunction with heat treatment parameters adapted to cause the alloy to precipitation harden to the degree desired. Thus, the degree of heat and extent of dwell time may be varied in a particular wire in order to desirably manipulate the final mechanical properties of the wire.

In general, there is substantially one-to-one correspondence between the degree of precipitation hardening and the increase in yield tensile strength. In accordance with the invention, the heat treatment should be selected to effect a degree of precipitation hardening such that the tensile strength of the wire is increased between by about 20% to 60% of the tensile strength before hardening. In one example, a wire formed from MP35N alloy having a diameter of 0.009 inch and having been cold worked to a reduction of 54.2% had a yield tensile strength of 219,000 p.s.i. Upon heat treatment at 975° F. for 30 minutes, an identical wire had a yield tensile strength of 302,000 p.s.i., an increase of about 38%. In each case, the yield point was taken at the point where the stress/strain curve deviated 0.1% from the straight line portion of the stress/strain curve.

The heat treatment also serves to partially relieve the internal stress that had been developed in the cold working of the wire. It is important, when precipitation hardening the MP35N alloy, that the heat treatment be effected while the wire is in a cold worked condition. The wire then may be centerless ground to effect the reduced diameter at the distal segment of the shaft. It should be noted that the partial stress relief that results from the heat treatment facilitates the centerless grinding of the distal segment of the shaft to its reduced diameter. In the absence of any stress relief, the centerless grinding could result in a distorted ground section.

A shaft may be formed from the Elgiloy, 455PH and Sandvik 1RK91 alloys in essentially the same manner.

The 1RK91 alloy is considered to be a precipitation hardenable martensitic stainless steel alloy comprising, in percent by weight, about 10% to 14% chromium, between about 7% to 11% nickel, molybdenum between about 0.5% to 6%, cobalt up to about 9%, copper between about 0.5% to 4%, aluminum between about 0.05% to 0.6%, titanium between about 0.4% to 1.4%, carbon and nitrogen not exceeding 0.05%, with iron as the remainder and the content of any other element of the periodic table not exceeding 0.5%. More specifically, the chemical composition of the alloy designated as 1RK91 included, in percent by weight, 12.2% chromium, 8.99% nickel, 4.02% molybdenum, 1.95% copper, 0.33% percent aluminum, 0.87% titanium, 0.009% carbon, 0.15% silicon, 0.32% manganese, 0.13% phosphorous and 0.003% sulfur.

The alloy commercially designated as 455PH is a martinsitic stainless steel alloy that is precipitation hardenable by a single step aging treatment. The alloy is considered to comprise, in percent by weight about 11.0% to about 12.5% chromium, about 7.5% to about 9.5% nickel, about 0.8% to about 1.4% titanium, about 0.1% to about 0.5% columbium and tantalum, about 1.5% to about 2.5% copper, up to about 0.5% molybdenum, about to about 0.05% carbon, up to about 0.5% manganese, up to about 0.04% phosphorous, up to about 0.03% sulfur and up to about 0.5% silicon, with the balance consisting essentially of iron except for incidental impurities.

Figure 6:
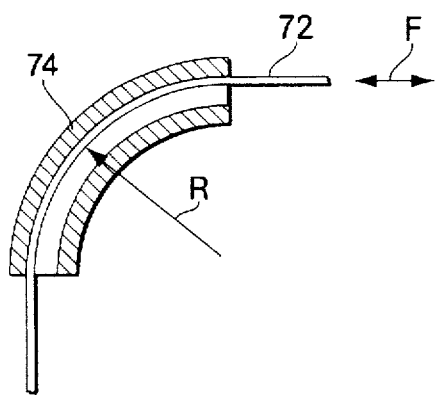
FIG. 6 is an illustration of a test fixture that may be used for comparative testing of the guidewires of the present invention with those of the prior art.
Figure 7:
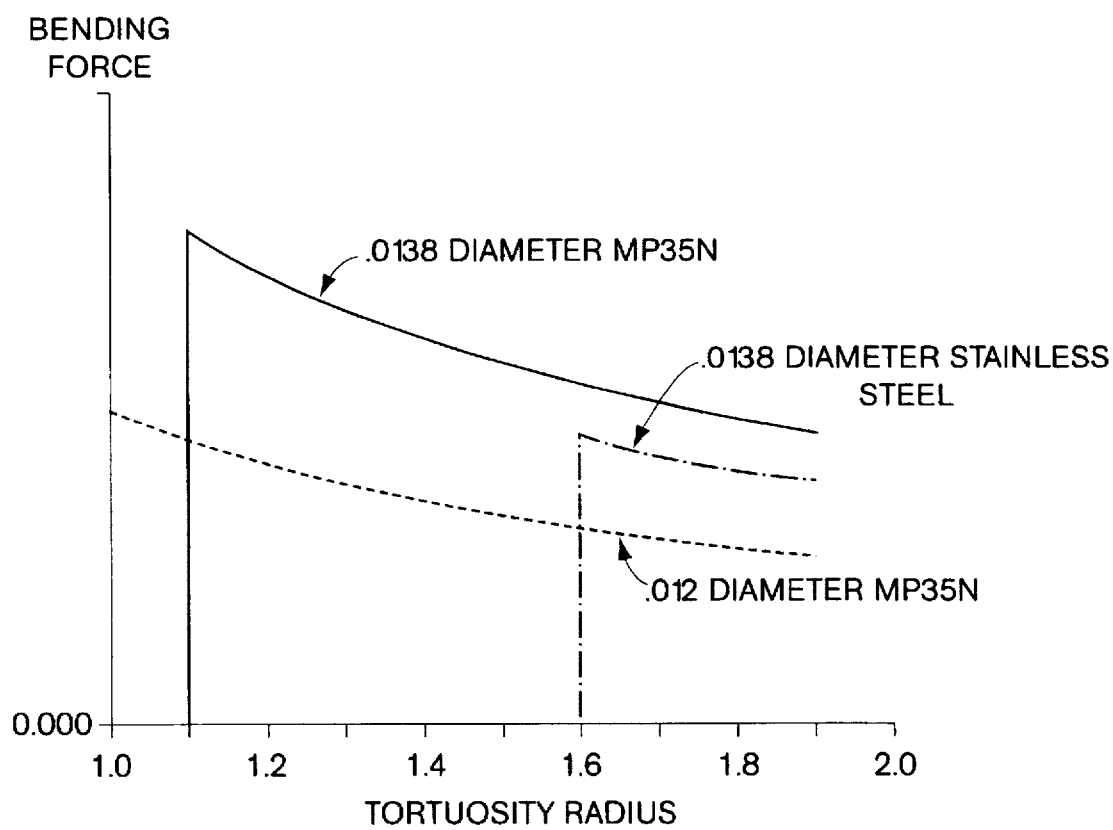
FIG. 7 is a graph diagrammatically illustrating the extended range of operation of guidewires made in accordance with the invention.

The increased kink resistance of a guidewire made in accordance with the invention is illustrated with reference to FIGS. 6 and 7. FIG. 6 depicts a test apparatus in which a wire 72 is pushed through an idealized simulated vascular curve 74 in which the force F required to push the guidewire through the simulated vessel is inversely related to the radius R through which the guidewire is advanced. FIG. 7 illustrates and compares, diagrammatically the performance of three guidewires including a cold drawn type 304 stainless steel wire 0.0138 inch in diameter, an MP35N alloy wire of the same diameter and an MP35N alloy wire in a smaller diameter (0.012 inch). The test apparatus of FIG. 6 was used to force wires through the apparatus as illustrated. The wires were each passed through a series of such simulated blood vessels having different radii and the force required to push the wire through the apparatus was measured. The comparative results are illustrated in FIG. 7 from which it can be seen that a 0.0138 inch diameter stainless steel wire failed when bent beyond a radius of 1.6 inches. In contrast, the same diameter wire formed from MP35N alloy, precipitation hardened in accordance with the invention, did not exhibit a tendency to fail until the bend radius was reduced to about 1.1 inches. Additionally, the force F necessary to advance the MP35N guidewire was greater than that of the same diameter stainless steel wire indicating that, notwithstanding its improved kink resistance, the MP35N wire, surprisingly, was also actually stiffer. A smaller diameter guidewire made from MP35N alloy (0.012 inch) was able to be passed through the apparatus of the radius of 1.0 inch without failing. The region on the graph that is disposed outside of the envelope defining the performance of the 0.0138 inch diameter stainless steel wire represents a region of a family of guidewires in accordance with the invention that can be expected to significantly outperform the prior art conventional designs with respect to available choices of stiff ness and kink resistance.

Figure 9:
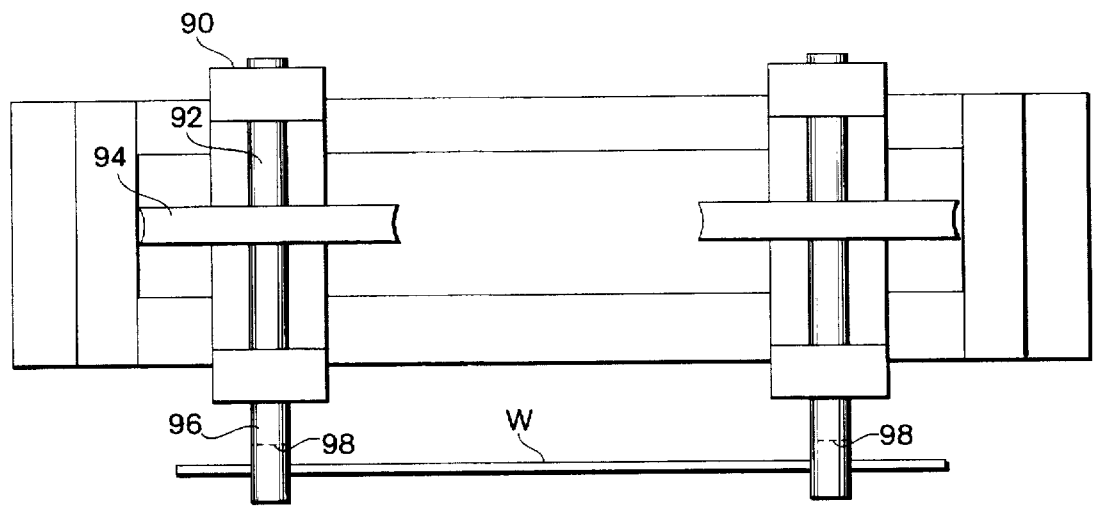
FIG. 9 is a plan view of the test apparatus as shown in FIG. 8.
Figure 8:
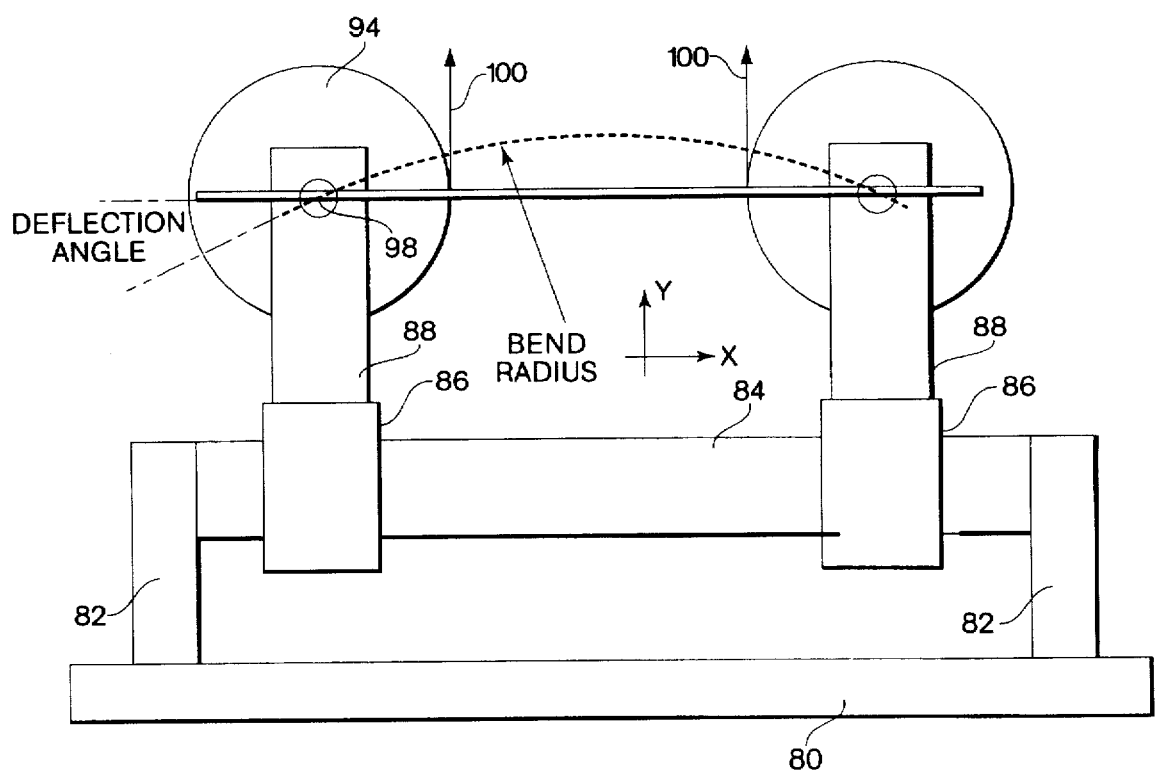
FIG. 8 is an elevation of a test apparatus for use in comparing the present invention with guidewires of the prior art.

FIGS. 8 and 9 illustrate a test apparatus that may be used to determine the degree of strain of a wire at its yield point. Such apparatus may be used to compare and distinguish guidewires of the present invention from those of the prior art. The apparatus is configured to subject the wire under test to a pure bending load. Test apparatus includes a rigid base 80 and a pair of rigid beam supports 82 secured to and extending upwardly from the base. The beam supports in turn support rigidly a support beam 84. A pair of carriages 86 are mounted on the beam for longitudinal movement along the beam. Carriages 86 are mounted using linear bearings of the "zero friction" type, for example, those in which the movable carriage 86 is maintained out of direct contact with the support beam by interposing a cushion of air under pressure. Each of the carriages 86 supports a pair of upstanding posts 88 having similar "zero" friction rotational bearings 90. Each pair of rotational bearings supports a shaft 92 to which a pulley 94 is secured. An end of each of the shaft 92 protrudes beyond one of the rotational bearings, as indicated at 96. The protruding portion 96 of the shaft 92 is provided with a suitable jaw or clamping arrangement to receive the sample wire W. For example, the longitudinal grooves 98 may be formed in the protruding ends 96 of the shaft to receive the ends of the sample wire W. A flexible belt or cable 100 is attached to each of the pulleys and is connected to a suitable loading machine, such as an Instron material tester (not shown). Operation of the test device develops a load P/2 at each pulley thereby loading the test specimen wire W by rotating and therefore bending the specimen. The mathematical product of the load P/2 and the pulley radius is the bending moment load on the specimen. Additionally, the rotation/deflection angle and/or the bend radius of the specimen provides the response of the specimen to the imposed bending load. Load versus deflection response data can be taken to characterize variation in the test specimens for comparison. The test apparatus can be used to determine guidewire resistance to permanent deformation (kinking). In the test procedure, the results using prior art guidewires is compared to that of wires manufactured in accordance with the invention by loading both wires and determining the bending load and bend radius at which the wires become permanently deformed into a circular arc. Prior art guidewires thus can be demonstrated to permanently deform at lower loads than those of the guidewires employed in the present invention.

The improved performance of the invention over guidewires of the prior art may be defined in a performance index (PI) that comparatively quantifies the performance of any diameter of guidewire shaft in a vascular tortuousity. Such index may be defined as follows:

$$PI = \frac{2R}{D_w}$$

where PI is the performance index, R is the smallest radius through which the wire will pass without permanent deformation and $D_w$ is the diameter of the wire. Lower values of PI for materials having the same inherent strength, will indicate greater levels of performance. Applying the foregoing to a 0.0138 inch diameter stainless steel wire represented in FIG. 6, the performance index A may be calculated to be 232. For the MP35N wire of the same diameter, the index may be calculated to be 159, indicating substantially greater level of performance. When comparing guidewires and the like made in accordance with the invention a reference to the performance index, it is important that the index be considered in conjunction with an indication of the inherent strength of the material on which the wire is formed, such as the modulus of elasticity of the material. For example, it is appropriate to compare the performance indices of stainless steel and MP35N wires in accordance with the invention because they have a modulus of elasticity that is comparable. Comparison of an MP35N wire with an identically dimensioned nitinol wire would result in the nitinol wire having a lower performance index because its pseudo-elasticity would enable it to pass through small radius bends without permanent deformation (low "R" value). The nitinol wire, however, has an inherently lower modulus of elasticity, of the order of 8,000,000 to 9,000,000 p.s.i. which accounts for some of the disadvantages that are encountered with nitinol wires.

In another aspect of the discoveries relating to the invention, it has been found that the heat treatment of the MP35N alloy, discussed above, results, unexpectedly, in an increase in the modulus of elasticity of the alloy. Depending on the temperature to which the alloy is heated during the heat treatment, the modulus of elasticity may be raised substantially from about 29,000,000 p.s.i., the modulus for the alloy before precipitation hardening. It may be possible to raise the modulus to as much as about 41,000,000 p.s.i., although at that level of heat treatment, the alloy may become somewhat brittle and not particularly suited for use as a vascular guidewire. It has been found that heat treatment to raise the modulus of elasticity to about 34,000,000 to 35,000,000 p.s.i. provides a guidewire that is well adapted for use in the vascular system. The phenomenon by which the modulus of elasticity of the alloy is raised is surprising and is not fully understood. It is believed that the phenomenon may result from the development, during the heat treatment, of one or more additional phases, having different crystalline structures with a higher modulus of elasticity such that when the average effect of all of the phases in the alloy are considered, the resultant modulus of elasticity is significantly increased.

It is expected that the Elgiloy alloy, also being an alloy of nickel, cobalt molybdenum and chromium, may display the same phenomenon.

From the foregoing, it will be appreciated that the invention provides new and improved guidewire construction in which the kink resistance of the guidewire is improved substantially without significant compromise of other desirable characteristics of the guidewire. The disadvantages of the prior art guidewires are avoided by forming a guidewire shaft from a material that has substantially less difference in the magnitudes of the compressive and tensile yield stresses (and corresponding yield strains) than had previously been available in the art. Moreover, a guidewire employing the invention may be made from a one-piece shaft that extends substantially the full length of the guidewire and has a modulus of elasticity at least as great as that of the stainless steel alloys that heretofore have been conventionally employed.

The advantages achieved by the invention also may be incorporated into the slender safety ribbons 61 at the distal tip of a guidewire that incorporates such ribbons. A safety ribbon formed in accordance with the invention similarly may display improved performance as compared to safety ribbons formed from more conventional materials, such as types 302 or 304 stainless steel.

Figure 10:
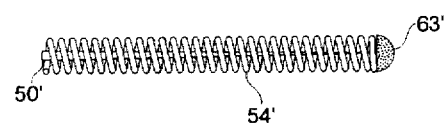
FIG. 10 is an illustration of the distal portion of a guidewire in which the core wire is attached to the distal tip of the coil at a tip weld.

Although the foregoing description of the invention has been in a context of a guidewire having a core wire that terminates short of the tip weld of the coil and is connected to the tip weld by a safety ribbon, guidewires also may be provided in which the core wire extends directly to and is incorporated into the tip weld 63, without the use of a separate shaping ribbon 61. FIG. 10 is a fragmentary plan view of the distal portion of such a guidewire in which the distal tip of the core wire is welded directly to the distal tip of the coil at the tip weld. The use of a tip weld to connect the tip of the core wire to the tip of the coil has become the method of choice for such connections because a welded joint has a higher strength and reduced likelihood of fracture than a joint that has been formed by adhesive, solder, or brazing.

Welded joints are made by melting the distal ends of the core wire and the coil and allowing the resulting pool of metal to solidify. This produces a joint containing a hemispherical bead as well as a heat affected zone. A distal segment of the core wire lies in this heat affected zone.

As described above in the prior art guidewires, the core wire, which is the primary load-bearing component of the guidewire, generally consists of a work-hardenable material such as type 304 stainless steel which is work-hardened prior to welding for increased strength. During welding, the distal segment of the core wire located in the heat-affected zone is annealed thereby greatly reducing the strength of such segment relative to the remainder of the core wire. Although the heat affected segment is work-hardenable, it is not possible to work the segment since this would damage the guidewire. Thus, the heat affected segment of the core wire is a weak link.

A heat-affected zone of the portion of the core wire of the guidewire (or the safety ribbon) that is immediately adjacent the bead 63' results from the high temperature of the welding process. At heat the distal portion of the guidewire immediately adjacent the tip weld (whether the core wire or shaping ribbon) may consist of a weldable material which can be precipitation-hardened from an annealed condition. Such materials are the precipitation-hardenable stainless alloys, such as 455PH stainless steel. Other stainless alloys which may be used include Elgiloy, MP35N and Sandvik's alloy No. IRK91, all discussed above. In the completed guidewire, the core wire 50' is in the precipitation hardened condition throughout.

The coil 54' consists of a weldable, preferably radiopaque material that is metallurgically compatible with the material of the core wire 50'. Among other things, metallurgical compatibility here means that an undercut in the core wire (or shaping ribbon) at the bead 63' can be at least largely avoided. Such an undercut tends to form during welding when the melting point of the coil exceeds the melting point of the core wire (or shaping ribbon). Preferred materials for the coil are the platinum alloys, especially 30 Au-70 Pt. A Pt-W alloy may also be used. The use of a non-radiopaque alloy such as type 304 stainless steel is also possible.

The bead 63' contains the materials of the coil 54' and the precipitation-hardenable material of the core wire 50'.

The guidewire is made as follows:

The core wire 50', which can initially be in the precipitation-hardened condition throughout, is inserted in the coil 54' and positioned so that the distal ends of the core wire and coil are at least approximately in register with one another. The distal ends of the core wire 50' and coil 54' are then autogenously welded to one another, preferably by microfusion. During the welding operation, the distal ends of the core wire and coil melt to form a molten mass. This mass solidifies upon completion of the welding operation to yield the bead 63'.

The welding operation also produces a heat affected zone adjacent to the bead 63', and a distal segment of the core wire 50' is located in the heat affected zone. This segment is annealed upon welding due to the high temperatures attained. As a result of annealing, the strength of the heat affected segment of the core wire 54' is reduced well below the strength of the unaffected part of the core wire 54'.

In order to increase the strength of the heat affected segment of the core wire, the welded joint including the bead and the heat affected zone is subjected to a heat treatment designed to precipitation harden the heat affected segment of the core wire. To this end, the welded joint is aged under conditions appropriate for precipitation-hardening of the material of the core wire. For instance, if the core wire consists of a precipitation-hardenable stainless steel, aging can take place at temperatures of about 350 to 550 degrees Centigrade. Aging will normally be completed within fifteen minutes but can be carried out for longer periods with temperature being more critical than time for the aging process. Following aging, the core wire 50' is in the precipitation-hardened condition throughout and the strength of the heat affected segment of the core wire is much closer to that of the unaffected part of the core wire than before aging.

Welding of the core wire to the coil can be performed using an electric arc process such as TIC or microplasma welding, or a non-electric arc process such as laser beam welding.

It should be understood, however, that the foregoing description of the invention is intended merely to be illustrative thereof and that other embodiments and modifications may be apparent to those skilled in the art without departing from its spirit. Although the description of the invention has been in the context of an angioplasty guidewire, its principles may be usable in other wire-like devices that are subjected to relatively small radius bends. Additionally, although several alloys have been described as exemplary for use in the practice of the invention, other alloys and materials may display similar characteristics so as to function within the scope of the invention.

Having thus described the invention, what we desire to claim and secure by Letters Patent is:

1. A medical guidewire for use with a catheter comprising an elongate flexible shaft having a compressive yield stress that is not substantially disproportionate to its tensile yield stress.

2. A guidewire as defined in claim 1 wherein the magnitude of the compressive yield stress is greater than about 60% of the magnitude of the tensile yield stress.

3. A guidewire as defined in claim 1 wherein the magnitude of the compressive yield stress is greater than about 70% of the magnitude of the tensile yield stress.

4. A guidewire as defined in claim 1 wherein the magnitude of the compressive yield stress is greater than about 80% of the magnitude of the tensile yield stress.

5. A guidewire as defined in claim 1 wherein the magnitude of the compressive yield stress lies in a range that is between about 60% and about 85% of the magnitude of the tensile yield stress.

6. A medical guidewire for use with a catheter comprising an elongate, flexible shaft in which the degree of compressive strain and the degree of tensile strain at the yield point in bending are not substantially disproportionate.

7. A medical guidewire for use with a catheter comprising an elongate flexible shaft having a stress/strain curve in which the yield points in tension and compression are not substantially disproportionately located along the curve.

8. A medical guidewire for use with a catheter comprising an elongate, flexible shaft in which the degrees of compressive strain and tensile strain at the yield point are less disproportionate than in an identically dimensioned guidewire shaft formed from stainless steel that has not been precipitation hardened.

9. A medical guidewire for use with a catheter comprising an elongate flexible shaft that has a compressive yield stress that is greater than the compressive yield stress of an identically dimensioned shaft formed from stainless steel that has not been precipitation hardened.

10. A medical guidewire as defined in claim 9 further comprising the modulus of elasticity being greater than about 29,000,000 p.s.i.

11. A medical guidewire as defined in claim 9 wherein the modulus of elasticity of the guidewire shaft is greater than that of nitinol alloy.

12. A guidewire for use with a catheter comprising:
   an elongate flexible shaft formed from a precipitation hardened alloy.

13. A guidewire as defined in claim 12 wherein the alloy comprises an alloy of nickel, cobalt, molybdenum and chromium.

14. A guidewire as defined in claim 13 wherein the alloy comprises MP35N.

15. A guidewire as defined in claim 13 wherein the alloy further includes less than about 10%, by weight, iron.

16. A guidewire as defined in claim 15 wherein the alloy comprises Elgiloy.

17. A guidewire as defined in claim 12 wherein the alloy comprises Sandvik 1RK91.

18. A guidewire as defined in claim 12 wherein the alloy comprises a precipitation hardenable martensitic stainless steel alloy comprising, in percent by weight, about 10% to 14% chromium, between about 7% to 11% nickel, molybdenum between about 0.5% to 6%, cobalt up to about 9%, copper between about 0.5% to 4%, aluminum between about 0.05% to 0.6%, titanium between about 0.4% to 1.4%, carbon and nitrogen not exceeding 0.05%, with iron as the remainder and the content of any other element of the periodic table not exceeding 0.5%.

19. A guidewire as defined in claim 12 wherein the precipitation hardened alloy is formed from a martinsitic stainless steel alloy that is precipitation hardenable by a single step aging treatment and comprising, in percent by weight, about 11.0% to about 12.5% chromium, about 7.5% to about 9.5% nickel, about 0.8% to about 1.4% titanium, about 0.1% to about 0.5% columbium and tantalum, about 1.5% to about 2.5% copper, up to about 0.5% molybdenum, up to about 0.05% carbon, up to about 0.05% manganese, up to about 0.04% phosphorous, up to about 0.03% sulfur and up to about 0.5% silicon with the balance consisting essentially of iron except for incidental impurities.

20. A guidewire as defined in claim 19 wherein the alloy comprises 455 PH precipitation hardened steel.

21. A guidewire as defined in any one of claims 12–20 wherein the shaft has a tapered distal segment.

22. A guidewire as defined in claim 21 wherein the shaft is formed from a single continuous wire of said alloy.

23. A guidewire for use with a catheter comprising an elongate flexible shaft formed from an alloy having a modulus of elasticity no less than about 28,000,000 p.s.i. and a performance index less than 232, said performance index being determined by the formula $$PI = \frac{2R}{D_w}$$

wherein PI is the performance index, R is the radius through which the wire may be bent without plastic deformation sufficient to affect the straightness of the wire and $D_w$ is the diameter of the wire.

24. A guidewire as defined in claim 23 wherein the modulus of elasticity is between about 28,000,000 p.s.i. to about 35,000,000 p.s.i.

25. A guidewire as defined in either one of claims 1 or 6 in which the guidewire shaft has a diameter no greater than about 0.020 inches.

26. In a guidewire for use with a catheter, the guidewire having an elongate flexible shaft having a proximal end and a distal end and a helical coil attached to the distal end, with the distal end of the helical coil extending distally beyond the distal end of the shaft, the guidewire further having a safety ribbon disposed within the helical coil having its proximal end attached to the shaft and its distal end attached to the distal tip region of the coil, the improvement comprising the safety wire being formed so that it has a compressive yield stress that is not substantially disproportionate to its tensile yield stress.

27. In a guidewire for use with a catheter, the guidewire having an elongate flexible shaft having a proximal end and a distal end and a helical coil attached to the distal end, with the distal end of the helical coil extending distally beyond the distal end of the shaft, the guidewire further having a safety ribbon disposed within the helical coil having its proximal end attached to the shaft and its distal end attached to the distal tip region of the coil, the improvement comprising the safety wire being constructed so that the degree of compressive strain and the degree of tensile strain at the yield point in bending are not substantially disproportionate.

28. In a guidewire for use with a catheter, the guidewire having an elongate flexible shaft having a proximal end and a distal end and a helical coil attached to the distal end, with the distal end of the helical coil extending distally beyond the distal end of the shaft, the guidewire further having a safety ribbon disposed within the helical coil having its proximal end attached to the shaft and its distal end attached to the distal tip region of the coil, the improvement comprising the safety ribbon being formed from a precipitation hardened alloy.

29. A guidewire as defined in claim 28 wherein the alloy comprises an alloy of nickel, cobalt, molybdenum and chromium.

30. A guidewire as defined in claim 28 wherein the alloy further includes less than about 10%, by weight, iron.

31. A guidewire as defined in claim 28 wherein the alloy comprises a precipitation hardenable martensitic stainless steel alloy comprising, in percent by weight, about 10% to 14% chromium, between about 7% to 11% nickel, molybdenum between about 0.5% to 6%, cobalt up to about 9%, copper between about 0.5% to 4%, aluminum between about 0.05% to 0.6%, titanium between about 0.4% to 1.4%, carbon and nitrogen not exceeding 0.05%, with iron as the remainder and the content of any other element of the periodic table not exceeding 0.5%.

32. A guidewire for catheters, comprising a casing; a core for said casing; and a junction between said casing and said core, the region of said junction including a precipitation-hardened material.

33. The guidewire of claim 32, wherein said junction comprises a weld.

34. The guidewire of claim 32, wherein said core comprises a wire of said precipitation-hardened material.

35. The guidewire of claim 32, wherein said casing comprises a helical coil.

36. The guidewire of claim 32, wherein said precipitation-hardened material comprises a stainless alloy.

37. The guidewire of claim 36, wherein said stainless alloy is 455PH stainless steel.

38. The guidewire of claim 36, wherein said casing is made of a stainless alloy.

39. The guidewire of claim 36, wherein said casing is made of a radiopaque alloy.

40. The guidewire of claim 37, wherein said casing comprises 30Au-70Pt alloy.

* * * * *